(12) United States Patent
Fischer

(10) Patent No.: US 12,582,456 B2
(45) Date of Patent: Mar. 24, 2026

(54) CRYOABLATION CATHETER ASSEMBLY, CRYOABLATION SYSTEM AND METHOD

(71) Applicant: afreeze GmbH, Innsbruck (AT)

(72) Inventor: Gerald Fischer, Völs (AT)

(73) Assignee: AFREEZE GMBH, Innsbruck (AT)

( * ) Notice: Subject to any disclaimer, the term of this patent is extended or adjusted under 35 U.S.C. 154(b) by 322 days.

(21) Appl. No.: 18/264,221

(22) PCT Filed: Feb. 3, 2022

(86) PCT No.: PCT/EP2022/052603
§ 371 (c)(1),
(2) Date: Aug. 3, 2023

(87) PCT Pub. No.: WO2022/167535
PCT Pub. Date: Aug. 11, 2022

(65) Prior Publication Data
US 2024/0032979 A1 Feb. 1, 2024

(30) Foreign Application Priority Data

Feb. 4, 2021 (EP) ..................................... 21155284

(51) Int. Cl.
*A61B 18/02* (2006.01)
*A61B 18/00* (2006.01)
(52) U.S. Cl.
CPC .... *A61B 18/02* (2013.01); *A61B 2018/00577* (2013.01); *A61B 2018/0212* (2013.01);
(Continued)
(58) Field of Classification Search
CPC .......... A61B 18/02; A61B 2018/00577; A61B 2018/0212; A61B 2018/025;
(Continued)

(56) References Cited

U.S. PATENT DOCUMENTS 3,630,203 A 12/1971 Sellinger et al.
5,758,505 A 6/1998 Dobak, III et al.
(Continued)

FOREIGN PATENT DOCUMENTS

EP 0 655 225 A1 5/1995
EP 0 726 734 A1 8/1996
(Continued)

OTHER PUBLICATIONS

International Search Report of PCT/EP2022/052603, May 23, 2022, 7 pages.
(Continued)

*Primary Examiner* — Ankit D Tejani
*Assistant Examiner* — Joshua Brendon Solomon
(74) *Attorney, Agent, or Firm* — Womble Bond Dickinson (US)LLP

(57) ABSTRACT

A cryoablation catheter assembly is described. The assembly comprises (a) an inlet for receiving an input flow of refrigerant fluid, (b) a cryo-applicator, (c) a flow splitter configured to split the input flow into a therapeutic flow portion and a precooling flow portion, and (d) a precooling arrangement configured to precool the therapeutic flow portion and guide the precooled therapeutic flow portion towards the cryo-applicator, wherein the precooling arrangement comprises a heat exchanger configured to apply an adjustable precooling power from the precooling flow portion to the therapeutic flow portion. Furthermore, a cryoablation system and a method are described.

16 Claims, 8 Drawing Sheets

(52) U.S. Cl.
CPC . *A61B 2018/025* (2013.01); *A61B 2018/0256* (2013.01); *A61B 2018/0262* (2013.01)

(58) Field of Classification Search
CPC .... A61B 2018/0256; A61B 2018/0262; A61B 2018/00023; A61B 2018/00041; A61B 2018/00714; A61B 2018/00797; A61B 2018/00821; A61B 2018/0237; A61B 2090/064
See application file for complete search history.

(56) References Cited

U.S. PATENT DOCUMENTS

| | | | |
|---|---|---|---|
| 6,074,572 A | 6/2000 | Li et al. | |
| 6,991,630 B2 | 1/2006 | Ryba | |
| 7,004,936 B2 | 2/2006 | Ryba et al. | |
| 8,387,402 B2 | 3/2013 | Littrup et al. | |
| 10,004,550 B2 | 6/2018 | Ryba et al. | |
| 2005/0159735 A1* | 7/2005 | Walton | F25D 3/10 606/22 |
| 2009/0124972 A1* | 5/2009 | Fischer | A61B 18/02 604/113 |
| 2012/0116393 A1* | 5/2012 | Jimenez | A61B 18/1492 606/42 |
| 2013/0103020 A1 | 4/2013 | Levin | |
| 2015/0300569 A1* | 10/2015 | Baust | F17C 5/02 62/50.1 |
| 2016/0038212 A1 | 2/2016 | Ryba et al. | |

FOREIGN PATENT DOCUMENTS

| | | |
|---|---|---|
| EP | 1 129 670 A1 | 9/2001 |
| EP | 1 357 847 A1 | 11/2003 |
| EP | 1 467 668 A1 | 10/2004 |
| GB | 1108905 A | 4/1968 |
| WO | WO 95/13025 | 5/1995 |
| WO | WO 02/058576 A1 | 8/2002 |
| WO | WO 03/061496 A1 | 7/2003 |
| WO | WO 2012/058153 A1 | 5/2012 |

OTHER PUBLICATIONS

Extended European Search Report of EP 21155284.9, Jul. 21, 2021, 10 pages.

Fischer, et al., "Impedance and conductivity of bovine myocardium during freezing and thawing at slow rates—implications for cardiac cryo-ablation", Medical Engineering & Physics, vol. 74, p. 89-98, Dec. 2019.

* cited by examiner

CRYOABLATION CATHETER ASSEMBLY, CRYOABLATION SYSTEM AND METHOD

This application claims the benefit of the filing dates of European Patent Application No. 21155284.9, filed on Feb. 4, 2021, and International Patent Application No. PCT/EP2022/052603, filed on Feb. 3, 2022, both of which are hereby incorporated by reference.

TECHNICAL FIELD

Exemplary embodiments of the present disclosure relate to the field of medical devices. More specifically, exemplary embodiments of the present disclosure relate to a cryoablation catheter assembly, a cryoablation system and a method.

BACKGROUND

Cryoablation or cryosurgery is the controlled modification of tissue by application of extreme cold. For example, for treating cardiac rhythm disorders electric pulse conduction in arrhythmogenic tissue is interrupted by freezing. For the treatment of hypertension, the activity of neurons involved in blood pressure regulation is reduced by freezing. In particular, for invasive and non-invasive applications, it is an important consideration that the size of cryoprobes or cryo-catheters is kept small. Methods for precooling refrigerant for size reduction by efficient use of refrigerant are described in the art (EP 1 357 847, U.S. Pat. No. 6,074,572). Here, the amount of mass flow across a therapeutically active portion of a device is an important design parameter influencing spatial dimensions.

Methods for precooling refrigerant to temperatures significantly below the freezing point of water inside an external device (e.g. a cryo-console) are described in U.S. Pat. No. 7,004,936. However, for such external precooling methods huge temperature gradients occur between the piping guiding the precooled refrigerant to the application site and ambient. This involves a significant loss of cooling power or requires substantial isolation rendering such methods impractical for single use disposables.

U.S. Pat. No. 6,991,630 describes a method for controlling a precooling flow and a therapeutic flow to a heat exchanger by using the same tank for supplying a precooling flow and a therapeutic flow in two separate lines. EP 1 467 668 and U.S. Pat. No. 10,004,550 describe the use of a therapeutic supply line and one or more additional precooling supply lines for allowing precooling heat exchange inside a catheter component (e.g., a handle or a shaft). This may allow for compensating warming of the refrigerant along the supply lines from a console towards a therapeutic target. However, using separate supply lines for precooling and therapeutic flow renders such a method incompatible with standard refrigerant connection lines. Furthermore, they require additional controllable mechanical valves. Solenoid valves, however, may warm a refrigerant. Furthermore, improper valve function may impose a safety risk in a medical application of a high-risk profile defining a need for safe design with a limited number of components exposed to mechanical wear.

Some methods described in the art utilize a single supply line for guiding a therapeutic flow portion and a precooling flow portion towards a cryoprobe or a cryo-catheter. EP 1 467 668 and U.S. Pat. No. 10,004,550 refer to Joule-Thomson (JT) based cryoprobes. Here, inside the cryoprobe (in a handle or a shaft structure), one or more narrow bypass orifices are foreseen in the supply line. Such orifices or micro-holes guide a precooling portion of the primary refrigerant such that it chills the therapeutic flow portion. However, while US discloses methods for temperature control of a therapeutic cryo-applicator, no means are provided, which allow for an adjustable or controlled splitting of refrigerant flow in a precooling portion and a therapeutic portion along a single supply line in situations of changing environmental conditions (ambient temperature, refrigerant supply pressure, thermal load on catheter, etc.).

U.S. Pat. No. 6,991,630 also describes the use of Peltier coolers inside a catheter handle. Such Peltier coolers may not allow for achieving precool temperatures significantly below 0° C. Furthermore, they may be economically unattractive in disposable devices. U.S. Pat. No. 5,758,505 describes a miniaturized heat exchanger structure for cryogenic applications (i.e., for coolants allowing for extremely low cryoprobe temperatures well below −100° C.). Here, the backstream of the therapeutic flow is used for precooling a supercritical fluid such that upon pressure reduction a mixed phase fluid is obtained. No splitting of the flow is foreseen, and no control mechanism is disclosed. The low temperatures achieved by this technique may cause safety issues and/or unintended freezing of adjacent tissue. Furthermore, high supply pressures needed for supercritical supply may involve safety issues.

U.S. Pat. No. 8,387,402 describes the use of supercritical or near critical fluids for achieving freezing temperatures well below −100° C. Beside the risk of unintendedly destroying adjacent tissue, this method requires near critical pressures also in the return pathway of the cryo-probe, thus, additionally involving the risk of burst or leakage.

As described by Fischer et al. ("Impedance and conductivity of bovine myocardium during freezing and thawing at slow rates—implications for cardiac cryo-ablation", Medical Engineering & Physics, 74:89-98, December 2019), relatively moderate low tissue temperatures, such as −5° C., may be sufficient for a safe generation of therapeutically efficient lesions in tissue.

There may thus be a need for improved precooling techniques that are effective, safe, reliable, simple, and compatible with a wide range of existing ablation equipment.

SUMMARY

This need may be met by the subject matter of the independent claims. Further exemplary embodiments are set forth in the dependent claims.

According to a first aspect of the present disclosure, a cryoablation catheter assembly is provided. The assembly comprises (a) an inlet for receiving an input flow of refrigerant fluid, (b) a cryo-applicator, (c) a flow splitter configured to split the input flow into a therapeutic flow portion and a precooling flow portion, and (d) a preceding arrangement configured to precool the therapeutic flow portion and guide the precooled therapeutic flow portion towards the cryo-applicator, wherein the precooling arrangement comprises a heat exchanger configured to apply an adjustable precooling power from the precooling flow portion to the therapeutic flow portion.

This aspect of the present disclosure is based on the idea that an input flow of refrigerant fluid is split into a therapeutic flow portion and a precooling flow portion and that the precooling flow portion is used to precool the therapeutic flow portion within a precooling arrangement utilizing a heat exchanger capable of applying an adjustable precooling power from the precooling flow portion to the therapeutic flow portion before the latter is guided towards the cryo-applicator. Thereby, a close to optimal precooling of the therapeutic flow portion can take place within the catheter assembly itself over a wide range of ambient conditions. Hence, the precooling is precise and effective and does not require a separate supply of precooling fluid, e.g., through a separate dedicated supply line.

In the present context, the term "flow splitter" may in particular denote any structure capable of receiving an input flow (i.e., the input flow of refrigerant fluid) and outputting at least two separate flows (i.e., the therapeutic flow portion and the precooling flow portion).

In the present context, the term "adjustable precooling power" may in particular denote that the amount of precooling power is not fixed but dependent on other factors and influences. In particular, the term "adjustable" may denote that the precooling power may be actively and/or passively influenced and changed.

In the present context, the term "therapeutic flow portion" may in particular denote a flow portion that is dedicated to be used by the cryo-applicator to perform a desired cryoablation treatment to a selected area of tissue.

The heat exchanger comprises (a) a boiling chamber, (b) a conduit configured to guide the precooling flow portion from the flow splitter to the boiling chamber, and (c) a heat transfer structure in thermal contact with the boiling chamber and configured to guide the therapeutic flow portion.

The conduit guides the precooling flow portion from the flow splitter to the boiling chamber which is in thermal contact with the heat transfer structure through which the therapeutic flow portion is guided. Thereby, the temperature change (temperature drop) of the precooling flow portion within the boiling chamber results in the application of a corresponding precooling power to the therapeutic flow portion through the heat transfer structure.

The conduit comprises a flow impedance selected to maintain the precooling flow portion within a predetermined range.

In other words, the flow impedance is selected such that the part of the total refrigerant flow that is used for precooling, i.e., the precooling flow portion in relation to the total refrigerant flow, is within a predetermined range. Hence, by selecting the flow impedance in view of typical operating conditions, an effective precooling can be obtained. The flow impedance depends on several factors, including in particular the geometry and dimensions of the conduit.

According to an exemplary embodiment, the microtube has a cross-sectional area of $0.1$ mm$^2$ or less, and/or the microtube has a length of at least 5 mm.

According to a further exemplary embodiment, the microtube has an inner diameter of 90 μm and a length of 40 mm.

According to a further exemplary embodiment, the precooling arrangement comprises a temperature adjustment device configured to adjust the temperature of the precooling flow portion within the conduit.

By adjusting the temperature of the precooling flow portion within the conduit, the effective flow impedance of the conduit will change correspondingly due to the temperature induced change in density of the fluid. Thereby, the relation between precooling flow portion and therapeutic flow portion can be further adjusted. A particular advantage of this approach is that it works without any moving parts, such as valves or pressure reducers.

According to a further exemplary embodiment, the temperature adjustment device comprises an adjustable electric heating unit configured to heat the conduit.

The adjustable heating unit may in particular utilize an electrically conductive part, such as a wire wound around at least a part of the conduit, to heat the conduit when electric current flows through the conductive part.

According to a further exemplary embodiment, the temperature adjustment device comprises an adjustable heating and cooling unit configured to selectively heat and cool the conduit.

The adjustable heating and cooling unit may in particular utilize a Peltier element and provides even more flexibility by being capable of both cooling and heating the conduit—and thereby the precooling portion flowing therein.

According to a further exemplary embodiment, the assembly further comprises at least one temperature sensor arranoed and configured to provide a temperature signal indicative of the temperature of the therapeutic flow portion, wherein the temperature adjustment device is configured to adjust the temperature of the precooling flow portion within the conduit in dependency on the temperature signal.

In other words, the temperature signal is used as a feedback signal to regulate the temperature of the precooling flow portion.

According to a further exemplary embodiment, the at least one temperature sensor comprises a first temperature sensor arranged in or on the heat exchanger and adapted to sense a temperature of the precooled therapeutic flow portion leaving the heat exchanger. Additionally or alternatively, the at least one temperature sensor comprises a second temperature sensor arranged and adapted to sense a temperature of the precooling flow portion.

The first temperature sensor thus measures the temperature of the therapeutic flow portion after it has been precooled in the heat exchanger, while the second temperature sensor measures the temperature of the precooling flow portion. In an embodiment utilizing $N_2O$ as refrigerant fluid, the first temperature sensor would be expected to measure around $-30°$ C.

According to a further exemplary embodiment, the at least one temperature sensor comprises a third temperature sensor arranged and adapted to sense a temperature of the therapeutic flow portion within the cryo-applicator. Additionally, or alternatively, the at least one temperature sensor comprises a fourth temperature sensor arranged and adapted to sense a temperature of the therapeutic flow portion leaving the cryo-applicator.

The third sensor measures the temperature of the therapeutic flow portion within the cryo-applicator, i.e., at a stage where the fluid is delivering or has just delivered its cooling power to create the desired lesion, while the fourth temperature sensor measures the temperature on the low-pressure side of the cryo-applicator. Both temperatures provide valuable information, possibly in conjunction with other temperatures, such as those measured by the first and/or second temperature sensors, on the amount of cooling power delivered to the treated tissue and on the general state of the system, such as whether a leak has occurred.

In an exemplary embodiment utilizing $N_2O$ as refrigerant fluid, the third temperature sensor would be expected to measure a temperature between $-90°$ C. and $-80°$ C. while the fourth temperature sensor would be expected to measure a temperature between $-50°$ C. and $-20°$ C.

According to a further exemplary embodiment, the heat transfer structure has an elongate shape and extends through the boiling chamber.

The heat transfer structure may in particular be a cylindrical tube or similar passage extending through the boiling chamber such that the cooling power is conducted through the wall of the tube.

According to a further exemplary embodiment, a closing structure is arranged between the conduit and the boiling chamber, the closing structure being configured to adjust a flow cross-section in dependency of temperature.

The closing structure may in particular comprise an element that changes its shape in dependency of temperature, in particular in such a way that it reduces the flow cross-section with decreasing temperature.

According to a further exemplary embodiment, the heat exchanger is configured as a counter flow heat exchanger or as a parallel flow heat exchanger.

According to a further exemplary embodiment, the assembly further comprises a handle, wherein the precooling arrangement (and thereby the heat exchanger) is arranged within the handle.

According to a second aspect of the present disclosure, a cryoablation system is provided, the system comprising (a) a cryoablation catheter assembly according to the first aspect or any of the exemplary embodiments described above, and (b) a console configured to supply a flow of refrigerant fluid to the inlet of the cryoablation catheter assembly, wherein the console comprises a preconditioning unit configured to adjust a specific enthalpy of the refrigerant fluid to a predetermined value.

This aspect utilizes the advantageous cryoablation catheter assembly according to the first aspect in combination with a console capable of—in addition to supplying a flow of refrigerant fluid—preconditioning the refrigerant fluid to have a predetermined specific enthalpy. Thereby, it can be assured that the temperature of the refrigerant fluid entering the cryoablation catheter assembly is within a suitable range such that the precooling within the precooling arrangement is as effective as possible.

According to a further exemplary embodiment, the system further comprises a controller configured to determine the predetermined value in dependency on at least one measured temperature.

The at least one measured temperature may in particular be a temperature at an input or an output of the precooling arrangement.

According to a third aspect of the present disclosure, a method is provided. The method comprises (a) receiving an input flow of refrigerant fluid, (b) splitting the input flow into a therapeutic flow portion and a precooling flow portion, (c) precooling the therapeutic flow portion by applying an adjustable precooling power from the precooling flow portion to the therapeutic flow portion utilizing a heat exchanger, and (d) guiding the precooled therapeutic flow portion towards a cryo-applicator.

This aspect relates to a method corresponding to the function of the cryoablation catheter assembly according to the first aspect.

It is noted that exemplary embodiments of the present disclosure have been described with reference to different subject matters. In particular, some exemplary embodiments have been described with reference to method type claims whereas other exemplary embodiments have been described with reference to apparatus type claims. However, a person skilled in the art will gather from the above and the following description that, unless otherwise indicated, in addition to any combination of features belonging to one type of subject matter also any combination of features relating to different types of subject matter, in particular to combinations of features of the method type claims and features of the apparatus type claims, is part of the disclosure of this document.

The aspects defined above and further aspects of the present disclosure will become apparent from the examples of embodiments to be described hereinafter. However, it is explicitly noted that the present disclosure is not limited to the described exemplary embodiments.

DETAILED DESCRIPTION

Figure 1:
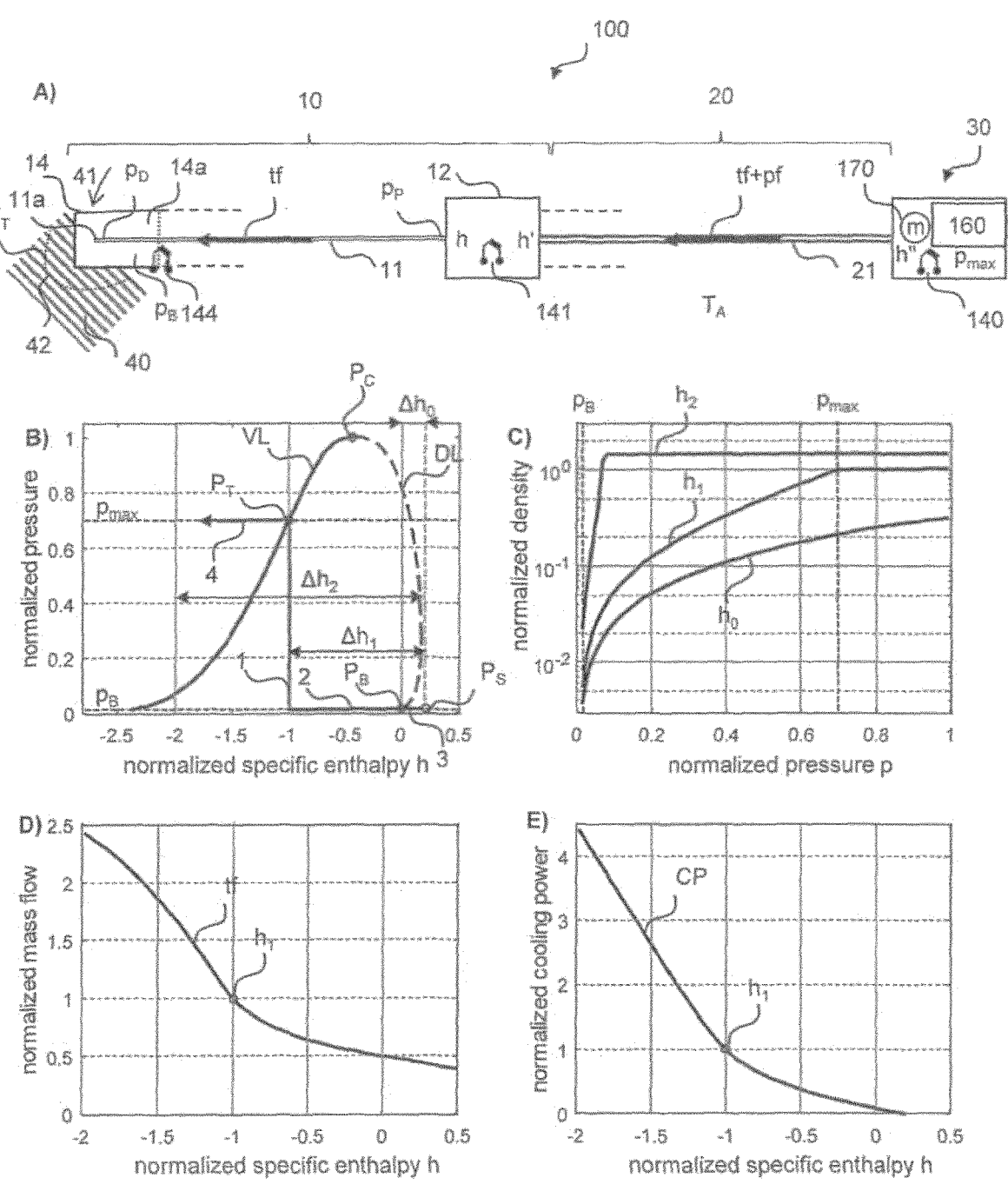
FIG. 1A shows an overview of a system according to an exemplary embodiment of the present disclosure.
FIG. 1B shows a pressure enthalpy phase diagram for the system shown in FIG. 1A.
FIG. 1C illustrates the density of refrigerant at various level of precooling for the system shown in FIG. 1A.
FIG. 1D illustrates a relation between flow and precooling level for the system shown in FIG. 1A.
FIG. 1E illustrates a relation between cooling power and precooling level for the system shown in FIG. 1A.
FIG. 1F illustrates a vapor pressure curve for a fluid.

The illustration in the drawing is schematic. It is noted that in different Figures, similar or identical elements are provided with the same reference numerals or with reference numerals which differ only within the first digit.

FIG. 1A shows an overview of a Joule-Thomson cooling system 100 comprising a controllable heat exchanger 12. The system 100 generally comprises a cryoprobe or cryocatheter 10 coupled to a cryo-console 30 that supplies refrigerant to the cryoprobe or cryo-catheter 10 via a connection or umbilical line 20. Refrigerant is stored inside the console 30 in a tank or closed loop cooling system (not shown). In the refrigerant supply lines the refrigerant is kept near a maximum operating pressure $p_{max}$. The refrigerant is delivered via a supply line at a flow rate tf+pf (therapeutic flow tf and precooling flow pf) towards the supply line 21 (component of the umbilical line 20) and further towards the catheter 10. For efficient operation, the console 30 may already partially or initially precool the refrigerant, such that it is in a liquid phase or mixed liquid/gaseous phase. However, in some exemplary embodiments the fluid flow tf+pf may be purely gaseous. In addition to the initial thermal preconditioning provided by the console 30, the total supply flow tf+pf is in heat exchange with an ambient having temperature $T_A$ and surrounding the supply line 21 or umbilical line 20. Thus, the cooling capacity or specific enthalpy h' of the refrigerant at the umbilical/cryoprobe junction is influenced by ambient conditions. It may be advantageous to provide a mechanism which compensates alternations in ambient conditions. Furthermore, varying operational conditions (e.g., varying heat exchange with the cryo-tip 14 with a target tissue 42) may require a control of cooling capabilities. This may be accomplished by using a heat exchanger 12 defining the specific enthalpy h in a proximal portion of tubing 11, which supplies the therapeutic refrigerant flow tf to the distal portions of the cryoprobe. The precooling flow portion pf may be used for adjusting the therapeutic flow tf effectively. The console may contain a preconditioning unit 160 adapted for adjusting h'. A temperature sensor 140 and/or a flow sensor 170 may be used in a control loop. Additionally or alternatively, a temperature sensor 141 may be foreseen inside the heat-exchanger 12. Furthermore, a temperature sensor 144 may be foreseen for measuring a temperature near the cryo-tip 14.

Figure 1F:
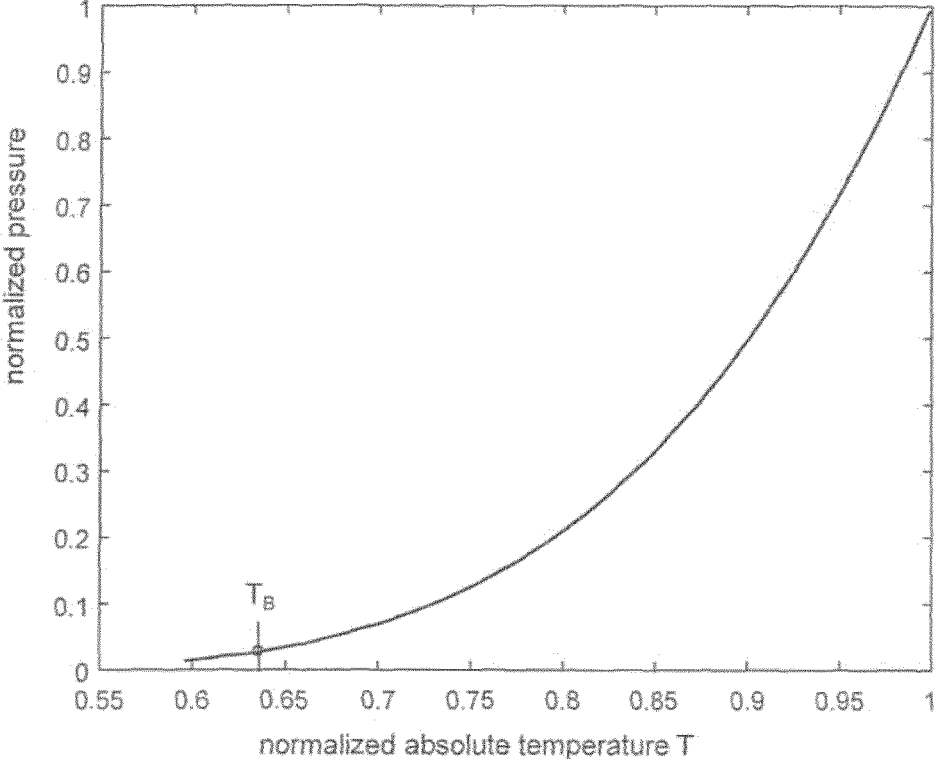

FIG. 1B shows a pressure enthalpy phase diagram (ph-diagram) for the refrigerant at the junction of the heat exchanger 12 with the therapeutic flow supply tube 11. As will become more apparent below, pressure and enthalpy are normalized accordingly such that the diagram applies to a broad group of coolants which can be used for Joule-Thomson cooling (such as nitrous oxide, freons, butane etc. for naming a few of them). Pressure is normalized by the pressure in a critical point Pc. A Joule-Thomson cooling system may be operated at maximum operating pressure $p_{max}$ well below the critical point pressure (i.e., $p_{max}<1$). A person skilled in the art will readily recognize that a coolant tank or reservoir (not shown) inside the console 30 may be used for providing refrigerant, and that a maximal pressure $p_{max}$ is defined by a tank temperature or ambient temperature. In other words, the refrigerant inside the tank is in a mixed phase state (partially liquid and/or partially gaseous) and, therefore, a vapor pressure curve as shown in FIG. 1F relates temperature and pressure. For "classical" Joule-Thomson cooling the liquid phase may be delivered from the reservoir (e.g., by using an eductor tube). Note that the liquid tank phase relates to a tank point $P_T$ on a vapor line VL. For illustration, the specific enthalpy h is normalized such that it equals one at a tank point $P_T$.

For "classical" Joule-Thomson cooling a coolant is delivered to a boiling volume or boiling chamber 14a within cryo tip 14. A throttle structure 11a (for example a narrow opening, a throttle, or a distal end of a micro-tube 11) may be used for further reducing the pressure down to a boiling pressure $p_B<<1$ along a process line 1. This boiling pressure $p_B$ may be near or even below an atmospheric pressure. Furthermore, it may be chosen somewhat above a triple point pressure of a medium for avoiding (partial) conversion of the refrigerant into a solid phase. Note that the process line 1 is within the mixed phase area (i.e., the area between the vapor line VL and the dew line DL). The gas content in the medium may continuously increase with decreasing h as the distance from the vapor line VL to the process line 1 increases with decreasing pressure. As can be seen from FIG. 1F, at (almost) isenthalpic pressure reduction from about tank pressure $p_{max}$ to boiling pressure $p_B$ induces a temperature drop down to a low boiling temperature $T_B$ and allows for cooling a target medium or target tissue 40 to substantial sub-zero temperatures. During boiling of the medium along process line 2 its specific enthalpy may continuously increase reflecting a further continuous increase of the gas content (the refrigerant boils out). At the point $P_B$ the process line 2 crosses the dew line DL. Here, the refrigerant has been converted to a saturated steam. We defined the specific enthalpy scale such that specific enthalpy h was zero at the low-pressure dew line point $P_B$. At the point $P_B$ the coolant temperature is near the boiling temperature $T_B$. It may be of advantage to select a coolant such that the boiling temperature is sufficiently low (e.g., below $-30°$ C. or more specifically below $-50°$ C.).

Boiling temperature may be significantly below a tissue temperature $T_T$ which defines the border 42 of lesion in the tissue 40. The lesion border temperature TT may be below $-2°$ C. or more specifically below $-10°$ C. Thus, by allowing the coolant to rewarm along process line 3 by some tens of degrees Centigrade above the boiling temperature, a small additional enthalpy $\Delta h_0$ can be used for cooling. As can be taken from FIG. 1B for the "classical" Joule-Thomson cooling cycle (process line 1 to 3) a total enthalpy $\Delta h_1$ can be delivered.

Using by way of example nitrous oxide as a refrigerant, at room temperature (near $20°$ C.) a normalized pressure $p_{max} \approx 0.7$ is obtained at the vapor line VL. By selecting the normalized boiling pressure $p_B \approx 0.014$ (i.e., near the atmospheric pressure) a boiling temperature near $-90°$ C. may be obtained. The normalized specific enthalpy $\Delta h_1$ may be near 300 J/g.

A person skilled in the art will readily appreciate that a broad spectrum of refrigerants is available. They may be composed from pure gases or gas mixtures and may be listed with "R-numbers". Thus, the choice of the refrigerant is not limited to nitrous oxide which was used here for illustration purposes. Essentially any refrigerant can be used with a normalized pressure near or below one at room temperature and a boiling temperature below $-50°$ C. or more specifically below $-70°$ C. at ambient pressure. For example, Freon 23 (R23) or Ethane may be used as a refrigerant.

A person skilled in the art will appreciate from the above that the delivered Delta in enthalpy can be increased by precooling the refrigerant from the tank point $P_T$ towards a lower enthalpy along process line 4. Here efficient solutions are needed for a) obtaining a shift to a low specific enthalpy h (e.g., $h<-1.3$ or more specifically $h<-1.6$) and b) adjusting h effectively to a desired value in the situation of varying ambient temperature $T_A$ or a varying thermal load imposed by an inconstant blood flow 41 onto the boiling chamber. Process line 4 is shown as an arrow for indicating this variable target. Along process line 4 the refrigerant is in its liquid phase and any decrease of enthalpy h will go along with a decrease of the refrigerant temperature. Any substantial decrease of enthalpy h will require a decrease in temperature by some or several tens of degrees centiarade and, thus, well below room temperature.

Therefore, precooling of the refrigerant to low specific enthalpy inside the console 30 (precooling level h") may go along with significant rewarming along the supply line 21 inside the umbilical line 20. The normalized enthalpy h' at a junction of the umbilical line 20 with the cryoprobe 10 may have, thus, increased again to values near one or even above one (due to the pressure drop along the supply pathway the boiling temperature may decrease below ambient temperature). Thermal isolation may render umbilical lines 20 bulky and expensive. A heat exchanger 12 as will be described in more detail below may be used for adjusting the enthalpy h at the junction of the heat exchanger 12 with the supply tube 11 for the therapeutic flow tf, thus, (over-) compensating rewarming.

FIG. 1C illustrates the density of refrigerant at various levels of precooling. Density was normalized by the density at the tank point $P_T$, i.e., density at unit normalized specific enthalpy (h=−1, or $h_1$) and tank pressure $p_{max}$ equals one.

Note that a semi-logarithmic scale was chosen for depicting the large variations in density over more than two orders of magnitude between the boiling pressure $p_B$ and the tank pressure $p_{max}$. It should be emphasized that the pressure drop from the tank pressure $p_{max}$ to the boiling pressure $p_B$ occurs along the entire supply pathway from the console 30 to the boiling chamber 14a (containing e.g., supply lines 11 and 21). Therefore, significant pressure variations occur in the supply lines and in particular within the distal supply line 11 which finally "throttles" the cooling medium to the boiling pressure $p_B$. Since density has a significant impact on the pressure drop in a flow pathway it significantly impacts on the amount of flow which can pass supply lines. At e.g., $h_2$ (i.e., h=−2) the coolant is in its liquid phase in a large portion of the pressure range and a large almost constant density is observed over a large portion of the pressure range [$p_B$ $p_{max}$]. Furthermore, density at the sample pressure level is always larger at a high precooling level $h_2$ compared to the reference level $p_1$. Thus, at comparable pressures the increase in density may also induce an increased flow along tubing 11. In contrast, at $h_0$ (i.e., h=0) the mixed phase coolant is close to a pure gaseous phase and density at $h_0$ is significantly reduced to the reference level. Thus, a reduced precooling level may also go along with a reduced flow along the tubing 11.

FIG. 1D shows a simulated flow tf along a micro tube 11 for varying precooling levels h. For simulations, at the proximal end of the micro-tube 11 its proximal pressure $p_p$ was set to 0.62. At the distal end of the micro-tube 11 its distal pressure $p_d$ was set to 0.03. A mixed phase flow simulation was performed at varying precooling levels h. For illustration purposes the simulated mass flow tf is normalized by the flow obtained at h=−1. Thus, the depicted result is independent of the actual dimensions of the micro-tube. The simulation was performed for the individual material properties of nitrous oxide. However, due to the normalization on both axes the result is a valid approximation for a broad range of coolants. As observed also from FIG. 1D, flow is continuously increased by precooling, i.e., by continuously shifting normalized specific enthalpy towards negative values.

FIG. 1E shows a simulated cooling power CP delivered along micro-tube 11 for a varying precooling level h. Cooling power is the product of Delta enthalpy (Δh as depicted in FIG. 1B) and the mass flow tf (as depicted in FIG. 1D). Cooling power CP was normalized by the cooling power obtained at h=−1. Thus, the result may be a valid approximation for different coolants and varying tubing geometry. Without being bound to a specific theory we observe that precooling has a double effect on the delivered cooling power: it increases the usable Delta enthalpy, and it increases the delivered flow.

This provides the following design opportunities/challenges:

For given tubing dimensions the delivered cooling power can be significantly increased by adjusting the precooling level inside a cryoprobe. This may be of particular interest when longer) elongated lesions must be created.

At a given cooling power, the dimensions of tubes (and thus potentially significant dimensions of a cryo-catheter) may be reduced. This may allow for miniaturization of cryo-devices in narrow spaced anatomical structures.

At a low specific enthalpy h, a small variation in enthalpy (for example due to varying ambient conditions) goes along with more pronounced variations in cooling power. Thus, proper measures must be foreseen for accurately adjusting/controlling cooling power.

The issues listed above apply particularly to the situation where a high cooling power or a significant miniaturization of dimensions is favorable. However, in certain situations like for example the ablation of a (relatively small) lung tumor the required cooling power may be relatively small (due to the low thermal load in a lung partially filled with air). In such a situation, a cryoprobe may be designed for working with essentially gaseous refrigerant (i.e., enthalpy h near zero). A person skilled in the art will readily apricate that the methods for precooling and cooling power adjustment disclosed in this document can be applied to a broad range of applications, including "high" and "low" power cooling.

It must be emphasized that controlled variation of a precooling level h may allow for wide range control of a cooling power at a near constant supply pressure level without a need for mechanical control structures such as valves inside a cryo-probe or cryo-catheter 10. As will be described in more detail below, one or more temperature sensors may be used for assessing thermodynamic function of a cryoablation system including: a sensor 140 inside the console 30, a sensor 141 inside the heat exchanger 12, a thermocouple or other temperature sensor 144 (see FIG. 5) in a draining portion of the system and a tip temperature sensor 145 (see FIG. 5). Furthermore, a flow sensor 170 may allow for assessing thermodynamic function of an ablation system for control purposes.

FIG. 1F displays a vapor pressure curve as it applies in a mixed phase condition of a fluid. The absolute temperature was normalized by the triple point temperature and pressure was normalized by a triple point pressure.

Figures 2A, 2B:
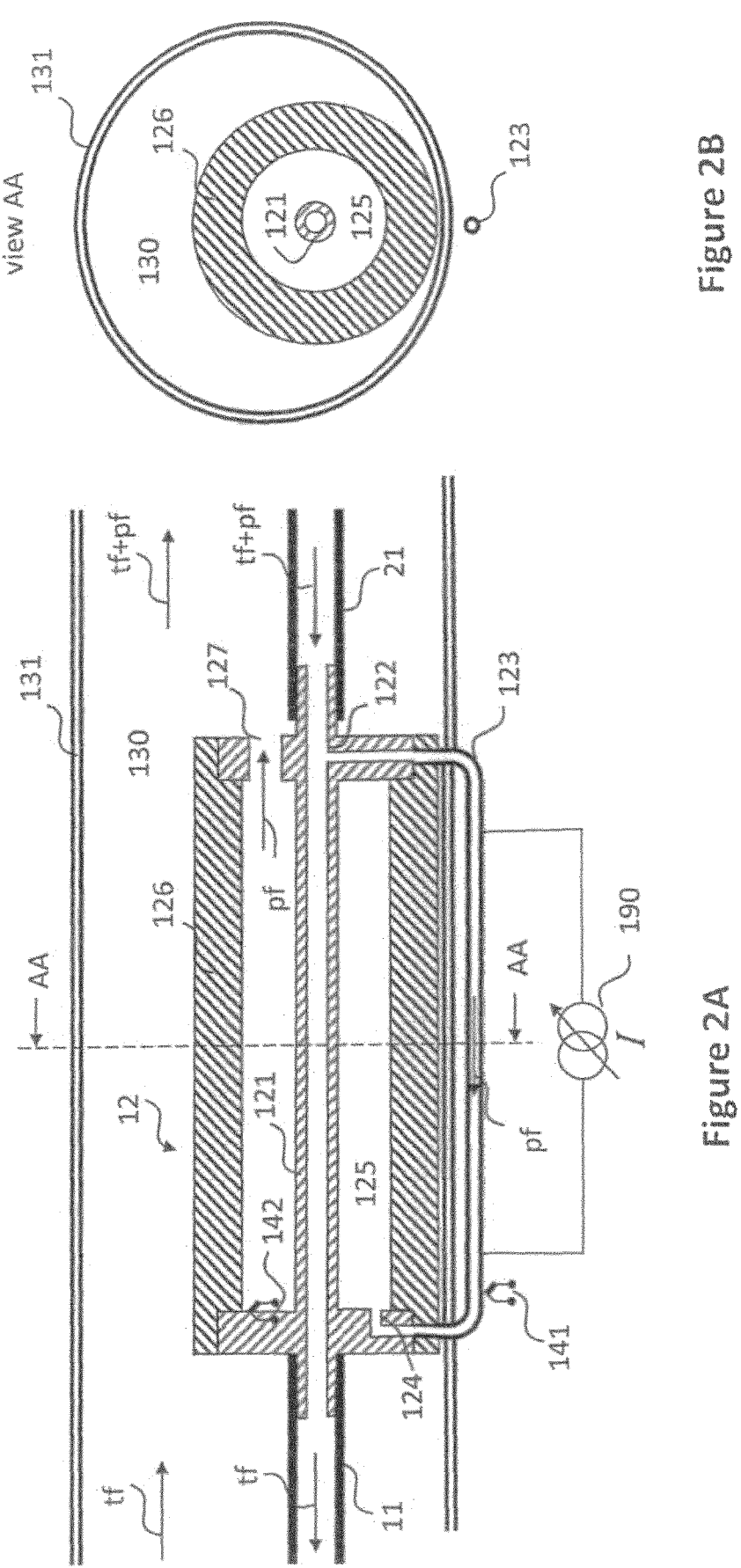
FIG. 2A shows a side view of a precooling arrangement according to an exemplary embodiment of the present disclosure.
FIG. 2B shows a cross-sectional view of the precooling arrangement shown 25 in FIG. 2A.

FIG. 2A and FIG. 2B show an exemplary embodiment of the adjustable/controllable heat exchanger structure 12. A supply tube 21 guides the total flow tf+pf towards the heat exchanger 12. Inside the heat exchanger 12 a heat transfer structure 121 is foreseen. It is made from a thermally conductive material such as for example stainless steel, copper, or aluminum. At a branching point 122 the refrigerant flow is split into a therapeutic flow portion tf and a precooling flow portion pf. The precooling flow pf is guided across a micro-tube 123. This micro-tube imposes a defined flow impedance which defines which ratio or percentage of the total flow is used for precooling. Firstly, geometric parameters such as the diameter and/or length of the micro-tube 123 define the flow impedance. Secondly, as will be described in more detail below, the temperature of the microtube may be altered for increasing or reducing the flow impedance. At a connection point 124, the precooling flow pf is guided into a heat exchange boiling chamber 125. Along the micro-tube pathway from the branching point 122 to the connection point 124 structures of narrow diameters (e.g., a nozzle or a throttle) may be foreseen for adjusting flow impedance. Additionally or alternatively, geometric properties such as a bending radius in the pathway may be tailored for obtaining a target flow impedance.

Inside the boiling chamber 125 the precooling refrigerant is allowed to boil out. It is guided back towards the low pressure drain. Thus, the heat transfer structure 121 provides a counter flow heat exchange configuration between the precooling flow pf and the therapeutic flow if. An isolation structure 126 reduces undesired heat flow to adjacent structures. The system can be designed such that the boiling chamber pressure is near but above the triple point pressure of the refrigerant. Thus, the boiling temperature is low, and the therapeutic flow portion can be precooled to temperatures significantly below zero degrees Centigrade, Thus, the therapeutic flow tf at the junction to the cryo-applicator supply tube 11 contains approximately the same cooling power as total flow tf-pf in the cryoprobe supply tube 21 (except for a small loss) but at a significantly reduced flow rate (as compared to the flow in umbilical tube 21).

At a throttle structure 127, the boiling chamber drains to the low pressure return lumen 130 defined by a low-pressure tubing 131, Here the flow portions tf and pf merge again. Thus, the low-pressure lumen 130 vents the entire flow to a scavenging system (693 in FIG. 5).

Inside the precooling bypass 123, the refrigerant may be in a liquid, gaseous or mixed phase condition. For example, it may be in a liquid phase at the branching point 122. As the refrigerant flows along the pathway, pressure continuously drops and in sections which are below the vapor pressure of the medium, it may be in a mixed phase. Under certain conditions, it may be even in a pure gaseous phase in distal portions of the precooling pathway (lowest pressure). As it is known from basic flow dynamics, pressure drop increases with decreasing density of a medium. Phase changes from liquid to mixed phase to gaseous go along with significant reduction in density amounting up to some orders of magnitude.

This strong non-linear dependence of pressure drop on the phase of the medium can be used for accurately adjusting the precooling flow. In one exemplary embodiment, it may be adjusted by proper choice of the geometric dimensions of the precooling pathway. For such an exemplary embodiment the precooling flow pf may be sufficiently well defined for a specified window of operation of a cryoablation system (for example ambient temperature range, tank pressure range, etc.). Furthermore, adjustment of a second precooling temperature inside the console may allow for sufficient control of flow and cooling power.

In another exemplary embodiment, the temperature of the micro-tube 123 may be altered for enhancing flow control. The microtube 123 may be heated by passing a controlled, adjustable electric current I across the tubing, thereby heating it by the ohmic loss. Such heating promotes phase change which increase the gas content in the precooling flow 112 and, thus, lower the precooling flow 112 without using moveable mechanical components. Thus, a high precooling flow is obtained without heating and it can be continuously reduced by continuously increasing the heating current I. A thermocouple 141 may be foreseen for monitoring the temperature of the microtube (for example in response to heating). Furthermore, a thermocouple 142 may be foreseen for monitoring the temperature of the heat exchanger structure (or the boiling chamber) as a surrogate for the temperature of the precooled therapeutic flow. As an option to heating by electric current, any other heat source as known in the art (for example a warm gas or liquid) can be used.

In yet another exemplary embodiment, the micro-tube 123 may be actively cooled (for example by a Peltier element or a cold fluid) for increasing the precooling flow by increasing the fluid density in the precooling micro-tube 123. All of these described measures can be combined for obtaining accurate control of the precooling flow pf in a wide range of operating conditions and, thus, for finally controlling the cooling power of a therapeutic cryo-applicator.

Referring now to FIG. 3A, another controllable heat exchanger structure 12 is shown. At a proximal connection 121$a$ (see FIG. 2A), a refrigerant flow tf+pf is supplied at a precool level h'. At the junction 122, the precooling flow is guided across a precooling microtube 123. At its proximal end, the precooling flow pf is guided along a connection 124 into a boiling chamber 125. Near a connection 124 there is a proximal pressure $p_{P'}$ and at a distal portion of tube 123 the is a distal pressure $p_{D''}$. Here, the refrigerant boils out near a low boiling pressure $p_B'$ and a heat transfer 150 is obtained relative to the therapeutic flow tf. This total heat flow 150 is a precooling power as used in FIG. 1 and it is defined such that withdrawing an inner energy from the therapeutic flow is counted positive. Thus, a positive valued heat flow/precooling power 150 reduces the precooling level h at a distal junction of the heat exchanger. An isolation structure 126 reduces heat losses pL to the ambient and seals the boiling chamber such that the boiling precooling flow pf is guided towards a draining opening 127. The cross-section of opening 127 may be selected such that a boiling pressure $p_B'$ inside the boiling chamber 125 may be significantly below a tank pressure $p_T$ but above a triple point pressure of the coolant.

FIG. 3B, FIG. 3C, FIG. 3D, and FIG. 3E display simulations obtained for precooling flow pf and precooling power PC delivered across the precooling microtube 123. For the simulations, a micro-tube length of 40 mm and a micro-tube inner diameter of 90 μm were chosen and nitrous oxide was used as a refrigerant. Normalized pressures were set to: $p_{P'}$ (proximal) 0.62 and $P_{D'}$ (distal) 0.03. For a precooling level of h'=1, a stationary precooling flow of 83 mgis and a stationary precooling cooling power of 16 W was predicted by simulations, Results were normalized analogous to FIG. 1B, FIG. 1C, FIG. 1D, and FIG. 1E, such that they apply to varying dimensions and different types of coolants. A person skilled in the art will readily understand that—depending on the scope of the actual design—actual dimensions can vary by orders of magnitude inducing also significant variation in flow and cooling power.

FIG. 3B and FIG. 3C depict the mass flow pf and precooling power PC assuming an essentially isenthalpic process path along the micro-tube 123, In other words, the heat flow from the micro-tube 123 to an ambient is small. An isolation structure 151 may be foreseen for providing sufficient thermal isolation. In certain exemplary embodiments the relatively small tube dimensions (diameter) may provide sufficient limitation of heat flow. Furthermore, in FIG. 3B and FIG. 3C, the heating power PH provided by a heat source 190 is assumed being zero. Similar as in FIG. 1D and FIG. 1E, flow and cooling power increase with decreasing enthalpy. However, the flow across tube depends on the enthalpy h' as delivered by the console 30 along the umbilical tube 20. Enthalpy h', therefore, depends on ambient conditions and a precooling level h" provided by the console. The proximal heat exchanger enthalpy h' may be assessed from a temperature sensor 141 or 142. Additionally or alternatively, a mass flow across the heat exchanger or the cryoprobe may be measured for assessing h'.

As can be taken from FIG. 3B and FIG. 3C, the precool flow pf across the heat exchanger 12 and the precooling power PC provided may be adjusted to a desired level by setting the proximal precooling level h' to a desired value. For compensating the undesired heat flow from the ambient, a preconditioning unit 31 (as described in more detail below)

may be foreseen inside or near console 30. If for example the heat flow 152 from the ambient to the umbilical line 20 increases, h" may be accordingly lowered for compensating this effect. Alternatively, if—by way of example—a higher cooling power is needed (e.g., near an organ of a high blood perfusion), also this can be achieved by adjusting h' to a lower value by decreasing h". Analogously, h' can be accordingly increased by increasing h" and by using sensors (temperature sensors 141 and/or 142 and/or mass flow sensors 170 as in FIG. 1 and FIG. 5).

In an individual design, proper choice of micro-tube dimensions, operating pressures and type of refrigerant may allow for control of coolant flow and precooling power in a sufficiently wide range by adjusting h", Thus, FIG. 3B and FIG. 3C refer to an exemplary embodiment where cooling power control is essentially provided by a preconditioning unit 31 inside or near a console Due to the heat losses 152 along the umbilical, it may be beneficial to design the system such that the proximal heat exchanger enthalpy h' is varied within an interval near h'=1. For example, h' may be chosen within an interval of −1.4 to −0.7 or, more specifically, it may be within an interval of −1.3 to −0.9, However, the heat exchanger may be designed such that the heat flow 150 may reduce the normalized specific enthalpy h of in a therapeutic flow coolant to values below −1.4 and more specifically below −1.6. As can been taken from FIG. 1E, the controlled adjustment of enthalpy h to sufficiently low values may allow for an efficient delivery of cooling power to a distal portion 14 of a cryoablation device 10 along a micro-tube 11.

The control range and control dynamics of a cryoablation system may be further improved by using a bypass control unit 190 for selectively modulating the flow pf across a micro-tube 123. For example, the micro-tube 123 may be made from an electrically conducting medium, such as stainless steel or brass or an electrically conducting plastic or other conducting material. By feeding an electrical current across a portion of micro-tube 123, an adjustable heating power HP can be delivered to the precooling flow pf. This heating power selectively increases the normalized enthalpy h' inside tube 123. The heating power HP reduces the density of the medium in a similar way as in FIG. 1C and, thus, the flow delivered across tube 123 at given pressure levels will decrease with increasing heating. Therefore, bypass heat has a double effect: it decreases the useable Δh in the precooling pathway and it reduces the precooling flow. Analogous to FIG. 1E, controlled adjustment of enthalpy h' may allow for wide range control of precooling power.

In FIG. 3D and FIG. 3E, the precool flow pf and the precooling power PC is simulated for varying degree of heating. We considered various levels of preconditioning h' and illustrated this by parametric plots. Note that a positive valued precooling power defines a heat flow away for the therapeutic flow while a positive valued heating power defines a heat flow towards the precooling flow. In the plots, precooling AND heating power are normalized by the precooling power which was obtained at a preconditioning level h'=1 at zero bypass heating (HP=0). As can be seen from FIG. 3E a, at preconditioning level h'=1.25, a normalized precooling power significantly above one (slightly above 1.7) is obtained without bypass heating (HP=0). At the same preconditioning level h'=1.25, a normalized heating power significantly smaller than one (slightly less than 0.6) is sufficient for reducing the precooling power to zero, Thus, a relatively small heating power can be used for controlling a much larger cooling effect. This will be further illustrated by an example below. Note that at high heating levels, precooling power becomes even negative reflecting the opposite definition of sign for heating power HP and precooling power PC.

Numeric Example 1

For further illustrating the control and design features which can be taken from FIG. 1A, FIG. 1B, FIG. 1C, FIG. 1D, FIG. 1E, FIG. 2, FIG. 3A, FIG. 3B, FIG. 3C, FIG. 3D, and FIG. 3E, a numeric example is provided. A cryoprobe 10 may be designed such that it delivers a nominal cooling power CP of 60 W to a tissue 40. Nitrous oxide $N_2O$ may be used as refrigerant. Inside the boiling chamber 14a, it may boil out at a boiling temperature near −85° C. At this nominal cooling power, the controllable heat exchanger 12 may precool the therapeutic flow tf to a normalized specific enthalpy h=−1.75 (approx. −35° C. for $N_2O$). Thus, a therapeutic flow of approx. 0.2 g/s is delivered across the tubing 11. As can be taken from FIG. 1D and FIG. 1E, this corresponds to a normalized flow of 2.2 (unit therapeutic flow 0.088 g/s) and a normalized cooling power of 3.6 (unit cooling power 16.9 W). In order to allow for efficient precooling, the console may deliver preconditioned refrigerant (therapeutic flow tf plus precooling flow pf) such that at the junction 122, a normalized enthalpy h'=−1.25 (approx. +5° C. for $N_2O$) is achieved. The simulations predict that for precooling the therapeutic flow, a precooling power PC of 15.4 W is needed. Thus, a precooling flow pf of approx. 0.067 g/s is delivered across the bypass tubing 123. As can be taken from FIG. 3B and FIG. 3C, this corresponds to a normalized flow of 1.44 (unit therapeutic flow 0.046 g/s) and a normalized cooling power of 1.75 (unit precooling power 8.8 W). In total, a mass flow tf+pf of approx. 0.27 g/s is delivered by the console 30.

In certain operational conditions it may be of advantage to reduce cooling power in a controlled fashion. In one exemplary embodiment this may be accomplished by heating the bypass pathway 123 using a current source 190. As can be taken from FIG. 3E, a normalized heating power of 0.57 reduces the precooling power PC delivered along the pathway 123 to zero. This corresponds to an absolute heating power of 5.0 W in the numeric example above (numeric example 1). By adjusting precooling power to zero as in this example, the enthalpy h of the therapeutic flow tf will approximately equal the enthalpy h'=1.25 at the junction 144. As can be taken from FIG. 1E a normalized therapeutic power 1.75 is delivered at h=1.25 which equals to an absolute cooling power of 29.5 W. In other words, by applying a heating power of 5 W at the bypass structure 123, the cooling power at the tip of the cryoprobe can be reduced by 30.5 W. A person skilled in the art will readily appreciate that a continuous variation of a relatively small heating power or more generally bypass heat flow (heating and cooling), may allow for a continuous adjustment or control of a larger cooling power at the tip of a cryo-probe or cryo-catheter 10. Note the analogy of such a configuration with an electric transistor. However, here the heat exchanger 12 in communication with a cryo-applicator 14 and a cryo-console 30 acts as a thermodynamic transistor.

In yet another exemplary embodiment a variation in preconditioning may be combined with a variation in bypass control. For example, in the numeric example described above, cooling power may be further reduced by increasing enthalpy h to one (i.e., less cooling by the preconditioner). At h=−1 cooling power is reduced by 43.1 W when adjusting bypass heat flow to zero. Due to the larger enthalpy level in the coolant supplied by the console 30, a heating power of only 4.2 W is needed for adjusting the bypass precooling power to zero. As can be seen from FIG. 1E, cooling power can be further reduced to near zero by further increasing enthalpy h. The values listed in this numerical example are shown for illustration and a person skilled in the art will readily understand that they can be generalized to a broad range of physical parameters.

In one exemplary embodiment, ambient conditions may vary within a relatively narrow band (e.g., a climate control room) and thermal load may be well defined within a certain range (e.g., a target vessel with a well-defined blood flow). Here, a preset adjustment may be made operating the system near approximately constant target parameters. However, in yet another exemplary embodiment, a higher degree of variation may be needed, and cooling power may be adjusted by using a preconditioning unit 31 and/or a current source or bypass control unit 190.

In yet another exemplary embodiment the heat transfer to the bypass control unit may be either positive or negative. This can be accomplished by using, for example, a thermo-electric (TE) element. A person skilled in the art will readily understand that by using a TE-element, the direction of the heat flow can be reversed by changing the polarity of the current flow.

Figures 4A, 4B, 4C:
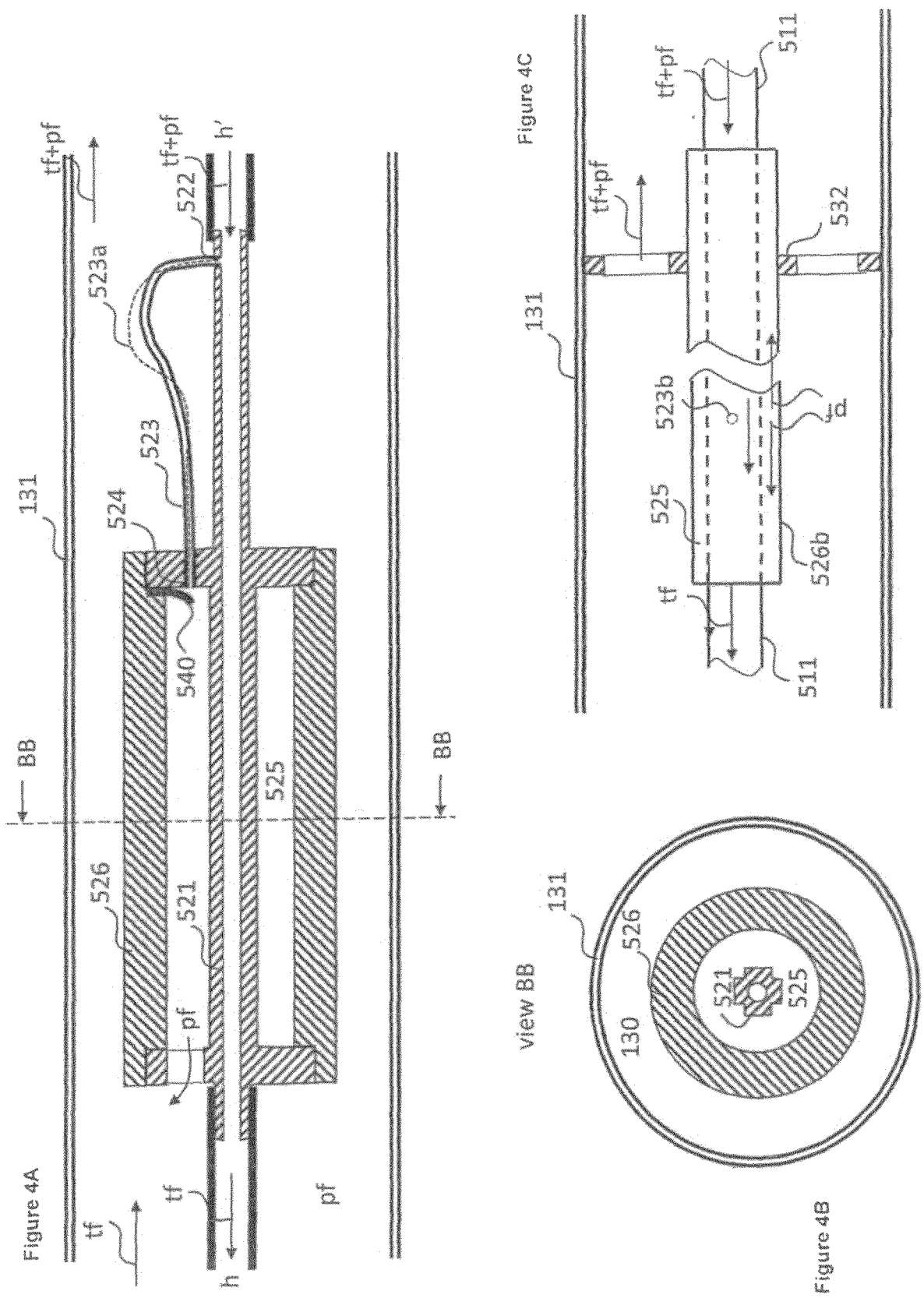
FIG. 4A shows a side view of a precooling arrangement according to another exemplary embodiment of the present disclosure.
FIG. 4B shows cross-sectional view of the precooling arrangement shown in FIG. 4A.
FIG. 4C shows a side-view of a precooling arrangement according to yet another exemplary embodiment of the present disclosure.

Referring now to FIG. 4A and FIG. 4B, another exemplary embodiment of the present disclosure is shown. In this exemplary embodiment the heat exchanging structure 521 provides a parallel flow heat transfer configuration. Here, the branching point 522 separating therapeutic and precooling flow portions is arranged at a distal location from the heat exchanger. A microtube 523 is foreseen for guiding the flow towards the boiling chamber 525 inside the heat exchanger. For the exemplary embodiment shown, the bypass duct 523 is pre-curved. Thus, in addition to length and diameter of the tubing, the bends or curves in the flow pathway define the precooling flow delivered across this pathway 523 at a given enthalpy level and a given temperature profile along the pathway.

In certain exemplary embodiments, the bypass pathway 523 may be made from a shape memory alloy such as e.g., Nitinol. The shape of bypass 523 at room temperature may be preset by heat treatment of the tubing in production. An Austenite crystal structure of the shape memory compound may define this shape. When guiding a precooling flow along bypass 523, a significant decrease in temperature may trigger the transition of the crystal structure to a Martensite phase. In the Martensite phase a significant lengthening of the tubing may occur, and mechanical stiffness may decrease to a lower level. Thus, low temperatures may trigger a change of the pre-curved shape as indicated by trajectory 523a. Due to the increase of length and decrease of bending radius the flow across the bended bypass 523a may get reduced.

Thus, in the case of a first low level of enthalpy h' (e.g., due to a low ambient temperature), the change of the pre-curved shape during cooling may be quite pronounced. This effect may contribute to reducing the precooling flow to a desired level. On the other hand, in case of a second higher enthalpy level h' (e.g., due to a warmer ambient temperature), the change of the pre-curved shape may be less pronounced allowing for a higher precooling flow. Thus, the use of a material with temperature dependent mechanical properties may (partially) compensate thermal ambient conditions and may allow for the use of a pre-adjusted system in a relatively broad range of ambient conditions. Additionally or alternatively, a closing structure 540 may be foreseen, which is adapted such that it straightens at low temperature and narrows the flow cross-section at the bypass d boiling chamber junction 524. When straightening at low temperature, structure 540 may reduce the gap to junction 524, thus reducing flow by reducing the space which hosts the flow.

Here, materials such as bi-metals or shape memory alloys may be used. In yet another exemplary embodiment a controllable heat source (as depicted in FIG. 2A and FIG. 3A) may be used for controlling the precooling flow pf inside the bypass 523 or 523a.

In FIG. 4B a "cross-shaped" cross-section is chosen for the heat transfer structure 521 between the boiling chamber 525 and the lumen of the therapeutic flow tf. The cross shaped boundary increases the area which can be used for heat transfer from structure 521 to the boiling chamber 125 as compared to the arrangement depicted in FIG. 2B, During boiling, the gas content in the medium increases which in turn reduces the heat transfer at the boundary. An increase of area may be beneficial for obtaining sufficient heat transfer. In certain exemplary embodiments, radial heat transfer fins may be foreseen for further increasing heat transfer. In yet another exemplary embodiment, a rough surface structure may be chosen for enhancing heat transfer. The same measures which may be taken for increasing heat transfer at the outer boundary of heat transfer structure 521 in cross section BB may also be applied at its inner boundary.

FIG. 4C shows a simplified exemplary embodiment of the heat exchanger structure which may be of advantage when aiming to provide the heat exchange in a relatively distant portion of the catheter, like e.g., a catheter shaft. Here, the heat exchanger should be chosen small in diameter. A longitudinal design may be chosen for providing sufficient "interface area" for heat transfer. The inner supply tube 511 may contain one or more bypass nozzles 523b for guiding a precool flow portion towards a boiling lumen 525 located in between supply tube 511 and an isolation tube 526b. Along the heat exchange portion (hatched lines), the precooling medium is allowed to boil, thereby cooling the therapeutic flow. Depending on the location of opening(s) 523b, the heat exchange configuration may be a counterflow configuration or a parallel flow configuration or a combination of both configurations. For a counterflow configuration opening 523b may be in a distal location and the distal gap between tubes 511 and 526b may be sealed. For a parallel flow configuration opening 523b may be proximal and the proximal gap may be sealed. A fixation structure 532 may be foreseen for adjusting the location of the isolation tubing 526b relative to the supply tubing. An outer vacuum tube 131 may define the common return pathway of boiled therapeutic refrigerant and boiled precool refrigerant towards a draining configuration.

Figure 5:
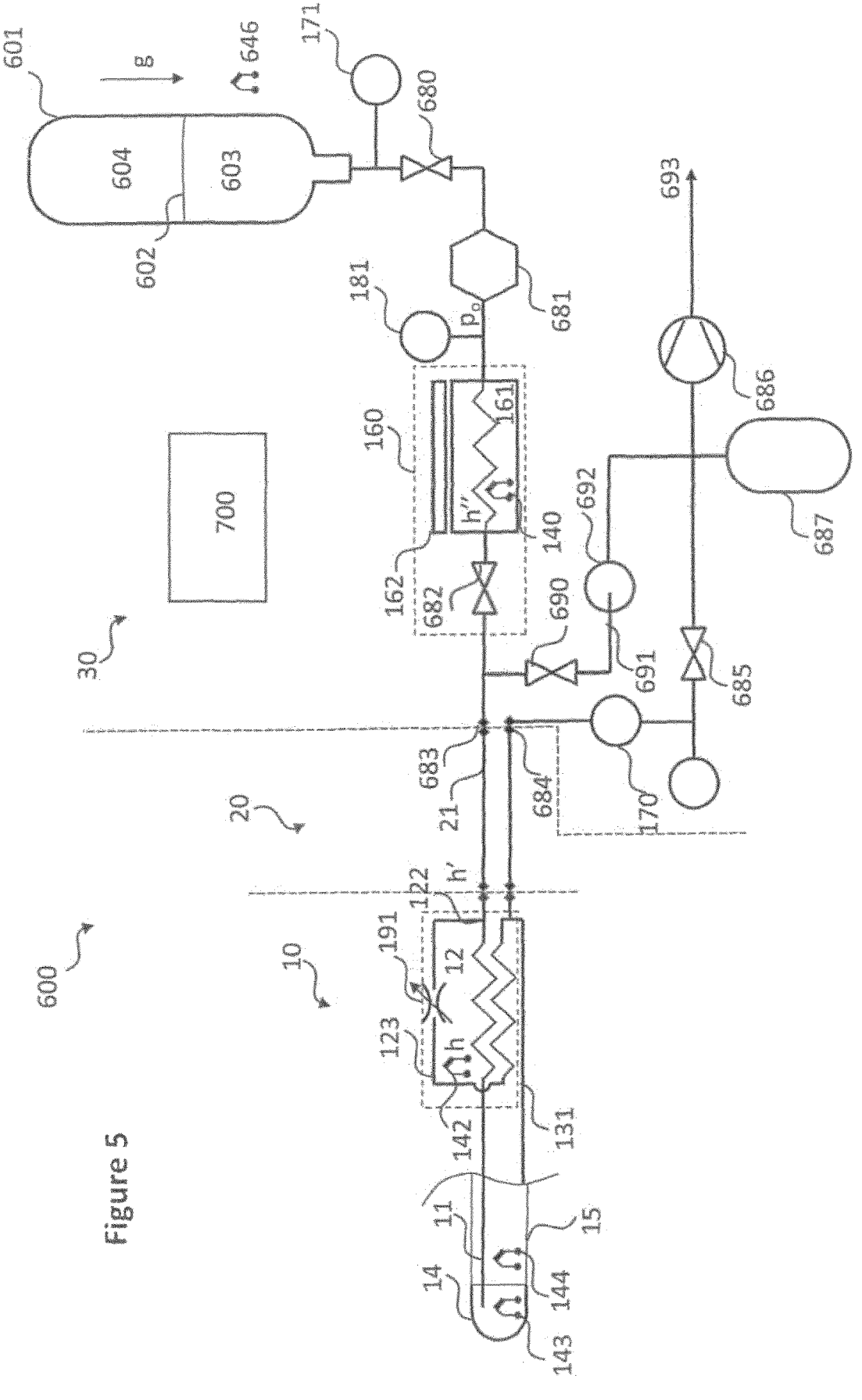
FIG. 5 shows a cryoablation system according to an exemplary embodiment of the present disclosure.

Referring now to FIG. 5, a controlled cryoablation system 600 with a bypass heat exchanger 12 is shown. The cryoablation system 600 contains a console 30, an umbilical line 20 and a cryo-catheter 10. A control system 700, such like a computer, may collect signals from a plurality of sensors. Based on these data and user input it may drive actuators (as explained in more detail below) for controlling the operation of the cryoablation system. A sensor 646 is used for assessing ambient temperature. The refrigerant is stored in a tank 601. For the depicted exemplary embodiment, the tank 601 is arranged such that its outlet is at the bottom of the tank 601. A filling level 602 is indicated, and the vector g shows the direction of gravity forcing the liquid phase 603 to accumulate at the tank bottom. The gaseous phase 604 is at the top of tank 601. For example, a cartridge like structure may be used as a tank. A pressure sensor 171 is foreseen for assessing the tank pressure. The tank temperature may be near an ambient temperature and the tank pressure may near a vapor pressure as it may be estimated from the vapor pressure curve as depicted in FIG. 1F. However, in certain situations, a measured tank pressure may significantly differ from a vapor pressure as estimated from room temperature. At a low filling level (e.g., when the liquid volume 603 inside the tank is much smaller compared to the gaseous volume 604), the tank pressure may drop quickly upon supplying refrigerant. This may be caused by an expansion of the medium inside the tank which shifts the actual pressure below the level of a thermodynamic equilibrium. Such a drop of pressure significantly below the pressure level estimated from ambient temperature may be used for detecting a low filling level of the tank.

A main valve 680 may be foreseen in the high-pressure duct right after the tank 601, The main valve 680 may be closed upon detecting a failure such as, for example, a leak in the high-pressure pipes. Furthermore, it may be closed during tank replacement for avoiding that the high-pressure pipes are discharged during replacement of the tank. A pressure reducer 681 may be foreseen along the high-pressure pathway. It may be adjusted such that its output pressure p 0 is somewhat (e.g., 10%) below a nominal tank pressure level. Thus, it may compensate (relatively small) pressure variations due to changes in tank temperature and filling level. For example, a decrease of tank pressure below a desired output pressure level, may indicate a low tank filling level. In certain exemplary embodiments the pressure reducer 681 may be preadjusted by mechanical means to a desired output pressure. In other exemplary embodiments, it may be an electronically controllable device. A pressure sensor 181 may be used for observing the output pressure.

A preconditioning unit 160 may be used for adjusting a specific enthalpy h" to a desired value. For the depicted exemplary embodiment, the preconditioning unit 160 comprises a heat exchanger 161 providing a heat flow from the refrigerant to a cooling structure 162, In certain exemplary embodiments this cooling structure may contain thermoelectric (TE) elements or Peltier coolers.

Figure 3:
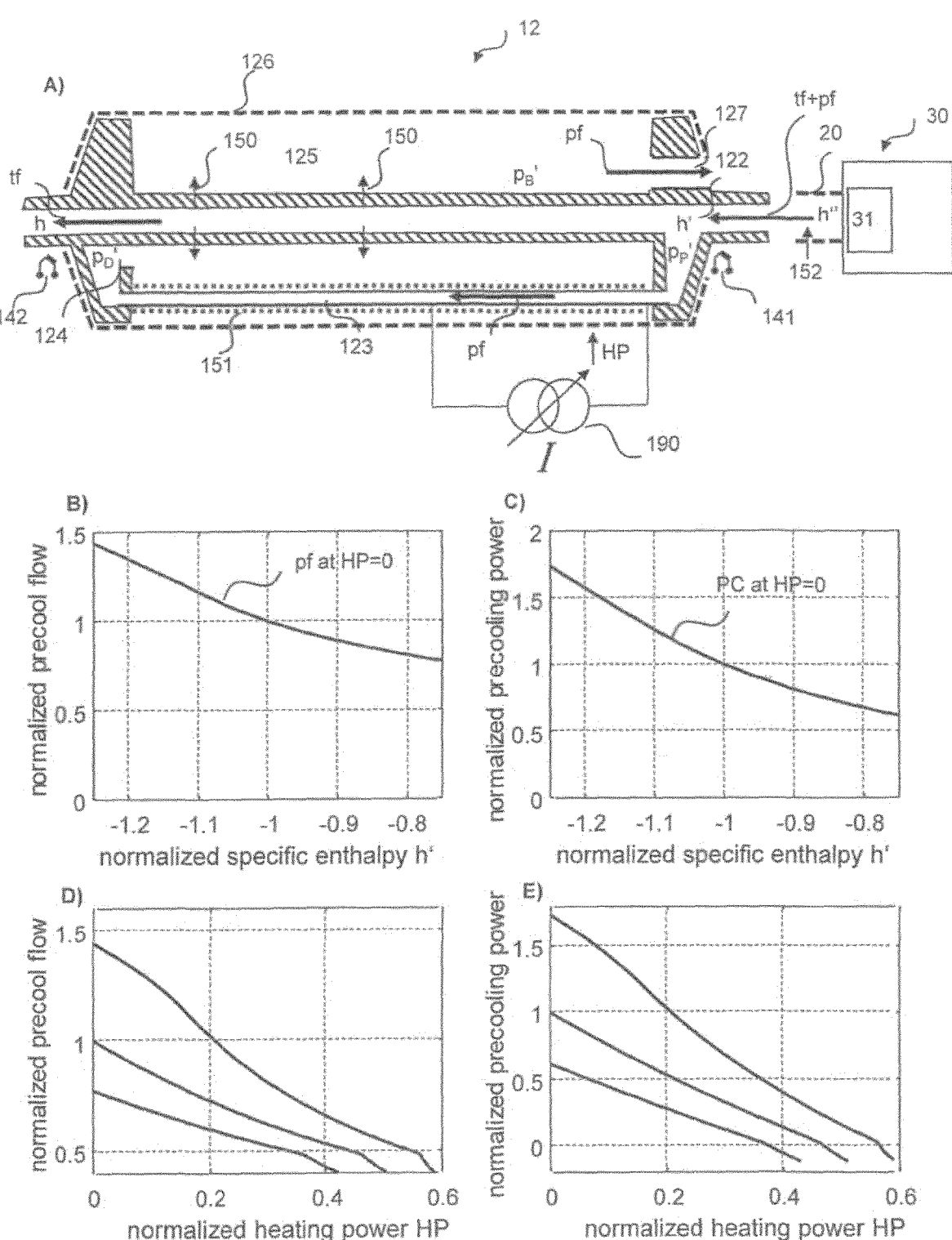
FIG. 3A shows a side view of a precooling arrangement according to another exemplary embodiment of the present disclosure.
FIG. 3B to FIG. 3E illustrate various simulations relating to precooling flow and precooling power for the arrangement shown in FIG. 3A.

TE-coolers provide a monotonic relation between a cooling power conducted away from the refrigerant and an electric current used for control. A person skilled in the art will readily appreciate that any other known cooling source, including compressor-based 3T refrigeration systems or Stirling coolers, may be used for component 162. Thus, component 162 may be used for adjusting enthalpy h' at a junction to the cryo-catheter indirectly by adjusting h". A temperature sensor 142 or 141 (as depicted in FIG. 3) may be foreseen for estimating h". In certain exemplary embodiments h" may be selected such that the refrigerant is in a purely or almost purely liquid phase at the output 683 of console 10.

A cooling valve 682 may be foreseen for selectively enabling/disabling refrigerant flow towards the catheter for therapeutic freezing. Note that the preconditioner is arranged in the high-pressure pathway such that the refrigerant gets also precooled in a standby operation mode between two freezes. This may allow for a quick cooldown of the cryo-applicator 14 at the start of a therapeutic freeze. During a freeze, the refrigerant is supplied along the high-pressure duct 21 of the umbilical line 20 towards the catheter. Along pathway 21 it may take up heat from the ambient, thereby (slightly) increasing specific enthalpy from h" to Note that by designing the system such that a target normalized specific enthalpy h' is near or somewhat below −1, temperature gradients to the ambient will be small easing the adjustment of h' by adjusting h". Furthermore, at preconditioning levels h" somewhat below −1 relatively small temperature gradients to ambient allow for effective use of TE-coolers. The cooling valve 682 may be mechanically integrated in a housing of the preconditioner 160 for compensating also heat losses of a solenoid inside the valve by cooling.

Inside the cryo-catheter 10 the high-pressure duct branches at connection point 122 into a therapeutic flow portion and a precooling flow portion. The splitting of the two flow portions may be adjusted as described above in conjunction with FIG. 2A, FIG. 3A, and/or FIG. 4A, FIG. 4B, and FIG. 4C. A variable flow thermodynamic flow impedance 191 may be foreseen for precisely adjusting or controlling flow. In certain exemplary embodiments the variable flow impedance may involve a heating structure 190 as described in FIG. 3A. In certain exemplary embodiments the variable flow impedance may be obtained from a mechanic control (523a and/or 540) as described in FIG. 4A. In certain exemplary embodiments combinations thereof may be applied. A temperature sensor 141 may be used for assessing or estimating the normalized enthalpy h of therapeutic flow tf. If, by way of example, the temperature in sensor 141 was too warm, it may be lowered by reducing flow impedance at 191 and/or by reducing the temperature in the preconditioner 160.

At the cryo-applicator 14 the therapeutic flow portion tf boils out. A temperature sensor 143 may be used for monitoring whether the desired boiling temperature may be achieved. If sensor 143 is placed near the junction of a supply line 11 with the boiling chamber, it may be located inside the boiling medium and, thus, will measure a temperature near the boiling point. However, a boiling medium is in a mixed phase and the measured temperature is almost independent of the actual gas content in the boiling medium. This may hamper the assessment whether the supplied cooling power matches the actual dissipated cooling power. In addition or as an alternative, a temperature sensor 144 may be placed in a back flow portion of a boiling chamber or at the distal catheter shaft 15. Thus, sensor 144 is located such that is in a portion of the back stream of the refrigerant where it has already fully or almost fully boiled out.

Since the heat capacity of gaseous refrigerant is low, the temperature at sensor 144 is sensitive to a mismatch of delivered and dissipated cooling power, Delivering too little cooling power is reflected by relatively warm shaft temperatures while delivering too much cooling power is reflected by low shaft temperatures, which are close to the boiling chamber temperature. If by way of example, shaft temperature 144 was too warm, it may be lowered by reducing flow impedance 191 and/or by reducing the temperature in the preconditioner 160. From a distal shaft portion 15 the gaseous therapeutic flow is guided back in the low-pressure duct. FIG. 5 illustrates the distal catheter portion by showing a geometric representation of the volumetric low-pressure duct 15 being arranged around a high-pressure supply 11. Note the benefits in safety of such a coaxial configuration. In case of a failure, such as a leak or a burst in the high-pressure lines, the refrigerant will be safely drained using the "shielding" of the low-pressure lines. The refrigerant return lines display a significantly larger cross section as compared to the supply lines due to the low density of the medium in the draining pathway.

The distal low-pressure pathway 15 is continued to a proximal low-pressure pathway 131. For providing a compact illustration, the proximal draining pathway 131 is shown as a line. However, as can be taken from FIG. 2A, and FIG. 4A to 4C, the coaxial design is maintained also in the proximal portion. Near the heat exchanger the gaseous therapeutic flow may merge with the gaseous precooling flow for being drained in a common lumen from the device. Note, however, that with heat exchanger 12 the precooling return flow is well separated from the therapeutic return flow. At the heat exchanger 12—despite some rewarming—the temperature of the gaseous therapeutic flow may still be well below ambient, reducing thermal losses in the heat exchanger. Note that in distal portions of a cryo-catheter or cryo-probe device, only the therapeutic flow portion is needed, thereby allowing for relatively small dimensions of components inside the body near the therapeutic target tissue. Merging flow in a distal device portion is less critical with respect to size, since such portions may be outside the body or the length of a merged flow pathway inside the body may be sufficiently small for keeping pressures in the draining pathway at sufficiently low levels.

Near the junction 684 of the draining pathway with the console, a flow sensor 170 may be foreseen. Note that for the shown exemplary embodiment, sensor 170 measures the sum of a therapeutic flow tf and the precooling flow pf. The product of this total mass flow with the preconditioning level h" as estimated, e.g., from the temperature at sensor 140, allows for estimating a total cooling power provided by the console and, thus, for controlling cooling. A vacuum valve 685 may be foreseen for selectively closing the draining pipes inside the console 30 in the case that no catheter and/or umbilical was attached and in the case of leakage. A vacuum pump 686 in combination with a windkessel 687 may be used for generating a stable low pressure drain. A short-circuit valve 690 is foreseen for quickly draining remaining refrigerant in the high-pressure duct to the low-pressure side at the end of each freeze. Thus, the short-circuit pass-way 691 allows for pronounced termination of freezing at the end of each cryo-application and in error conditions. A nozzle 692 may be foreseen for limiting the short-circuit flow to a maximal value. The refrigerant may be vented to a scavenging system.

In some exemplary embodiments an eductor tube may be used for obtaining a liquid refrigerant portion from the top off a tank. In yet another exemplary embodiment a closed loop refrigeration system may be foreseen. Such a closed loop system may use a compressor for re-pressurization of the drained refrigerant and a heat exchanger for re-liquifying it again at a temperature near an ambient temperature.

Numeric Example 2

For further illustrating the concept of control as depicted in FIG. 5, a numerical example is presented. A cryoablation system using nitrous oxide as a refrigerant may be designed for working at ambient temperatures in the range of +15° C. to +30° C. In this temperature range the absolute boiling pressure (see FIG. 1F) of nitrous oxide is 45.0 bar to 63.1 bar which corresponds to a normalized pressure of 0.62 to 0.87. For removing this dependence of pressure on ambient temperature from the system, the pressure reducer 681 may be preadjusted such that a normalized pressure near 0.6 is obtained at its output. This may allow for stable operation at varying ambient conditions and varying filling level.

In one exemplary embodiment the pressure reducer 681 may be pre-adjusted to work at a near constant pressure level. This pressure may be controlled allowing small variations of e.g., ±0.02 in normalized pressure. In yet another exemplary embodiment, the system may be configured to adapt this preset value by means of electronic control within a broader but still relatively narrow band of e.g., ±0.1 in normalized pressure. That may allow for configuration allowing to operate in a broader range of ambient conditions or at high/low filling levels.

Using again nitrous oxide by way of example, a preset normalized pressure of corresponds to a boiling temperature of +14° C. For ensuring that the refrigerant is entirely in its liquid phase, the preconditioner may be configured for precooling the refrigerant to a precooling temperature near +10° C. This corresponds to a normalized enthalpy h" of approximately −1.2. Note that here preconditioning is performed such that refrigerant temperature is below a boiling point but sufficiently close to room temperature for avoiding extensive rewarming along the supply pathway to the catheter.

In yet another exemplary embodiment precondition temperature may be adjustable in a range of e.g., zero to +15° C. In yet another exemplary embodiment the system may be adapted for heating the refrigerant for allowing operation in conditions of low thermal load. Note that by using for example TE-cooler in preconditioning unit 160 this can be achieved by reversing the polarity of the applied current.

Figure 6:
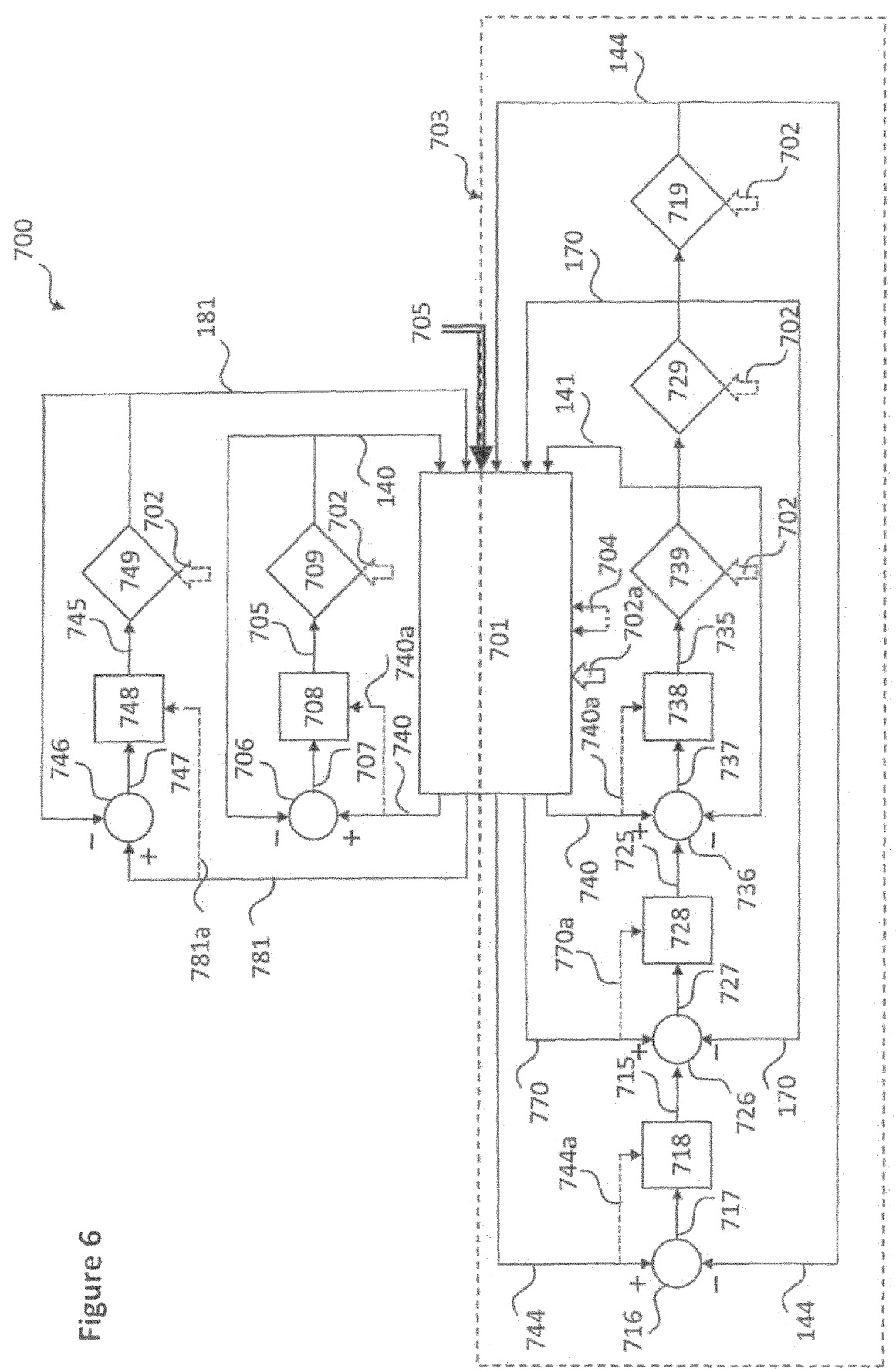
FIG. 6 shows a diagram of a control structure for a cryoablation system according to an exemplary embodiment of the present disclosure.

Referring now to FIG. 6, a schematic of a control structure 700 is shown. It contains a central control block 701. In certain exemplary embodiments, control block 701 may be realized by a computer program being executed on a controller or processor. Block 701 receives measured values via inputs, and outputs target values or setpoints to a plurality of sub-controlling units. The measured values involve parameters which are adjusted by control (like for example a mass flow 170) and parameters being not affected by control (as for example an ambient temperature $T_a$ or a tank pressure $p_\tau$).

The central control block 701 may preset or preadjust a target preconditioning temperature 740. This value may be passed to a negative feedback summation unit 706 where the difference 707 from the actual precondition temperature (i.e., the actual process value) 140 is computed. Based on this difference, a controller 708 sets an effector 709 for adjusting the actual preconditioning temperature. In an exemplary embodiment controller 708 may adjust an electric current (command 705) and a TE cooler 709 (as depicted in FIG. 5) may act as an effector. A person skilled in the art will readily appreciate that any known type of controller, as for example a PID controller or a non-linear controller type, may be used for implementing controller 708. In certain exemplary embodiments, controller 708 and feedback summation 706 may be implemented by a computer program.

The hashed pathway 740a indicates that the central control unit 701 may "overrule" the controller 708 and may set the controller command 705 (e.g., an electric current) directly in certain modes of operation, as for example during a "power-up" phase. In an exemplary embodiment, the system may be preadjusted for working at an essentially constant preconditioning temperature 140 by using a constant set point value 740 within a defined range of ambient conditions 702.

The depicted exemplary embodiment uses a three-stage cascade control 703 for properly adjusting a catheter target temperature 744. Value 744 may be a preset target for a catheter temperature such as, e.g., a distal shaft temperature 144 as shown in FIG. 5. For illustrating the function of this control block an event is considered, by way of example, which reduces the thermal load imposed onto the therapeutic section of the cryo-catheter. In such a situation an external component (e.g., a sheath or a balloon device) may (partially) cover the therapeutic catheter segment. That may reduce heat flow (i.e., less cooling power required) and the event may be reflected by an undesired decrease of a measured catheter temperature 144.

The central control block 701 pre-sets a target temperature 744. The negative feedback summation unit 716 quantifies the deviation 717 from the actual catheter temperature 144 and passes it to controller 718. Controller 718 generates a proper command 715 for adjusting a refrigerant mass flow (e.g., the sum of a precooling flow and a therapeutic flow). By way of example, a decrease of mass flow 170 may (re-) increase catheter temperature 144. A negative feedback summation 726 may process flow command 715, a preset flow 770 and the actual flow 170. It forwards the sum 727 to a flow controller 728. This flow controller 728 may generate a command 725. In some exemplary embodiments, command 725 may adjust enthalpy h in a heat exchanger 12 (as depicted in FIG. 5). By way of example, adjusting enthalpy h to more positive values may decrease flow. A negative feedback summation 736 may process the command 725, the preset enthalpy value 741 and the actual enthalpy 141 (as estimated e.g., by a temperature sensor inside a heat exchanger 12; see FIG. 5). The output of summation 737 is forwarded to the bypass controller 738 which generates a command 735. In some exemplary embodiments this command 735 may be an electric current I (as adjusted by current source 190 in FIG. 3A). An increase in current may heat a bypass structure 123 (as depicted in FIG. 3A) and may reduce refrigerant flow (as can be taken from FIG. 1E and FIG. 3E).

The actual physical dimensions and properties of an actual exemplary embodiment may relate a bypass command 735 to an estimated enthalpy 141 as is indicated by a heat exchanger plant 739 in the schematic. The response of the system may be assessed by measuring a precooling temperature. A preferred exemplary embodiment for measuring a precooling temperature may be a temperature 141 near a distal bypass section as shown in FIG. 2A and FIG. 3A. However, in some exemplary embodiments it may be more convenient to measure at a slightly different location, as for example sensor 142 in FIG. 2A and sensor 143 in FIG. 3A. Person skilled in the art will readily appreciate that any of these sensors may be used for estimating a temperature of the heat exchanger in control structure 700. As can be taken from FIG. 1E and FIG. 3E the precooling level of the refrigerant flow affects the measured total refrigerant flow 170 via a total flow impedance plant 729. The actual flow rate affects a catheter temperature 144 via a cooling power plant 719. While in a preferred exemplary embodiment catheter temperature may be a distal shaft temperature 144, a person skilled in the art will readily appreciate that in some exemplary embodiments other catheter temperatures, such as for example a boiling temperature 143, may be used. In an exemplary embodiment, controllers 718, 728 and 738 may be implemented by a computer program. However, in other exemplary embodiments at least one of the controllers in the systems may be implemented, for example, by an analog circuit. As indicated by the hatched lines 740a, 744a and 770a, the central controlling unit 701 may overrule feedback summation in certain conditions. For example, in an initial transient phase at the start of each freeze, one or more commands 715, 725 and/or 735 will be set directly by block 701.

Numerical Example 3

As was described above for the simulations in FIG. 3B, FIG. 3C, FIG. 3D, and FIG. 3E, an inner diameter of 90 μm and a length of 40 mm was assumed for the bypass pathway 123. Furthermore, it was estimated that a heating power of 5.0 W may cause a significant variation in therapeutic cooling power. It is assumed by way of example that, like in FIG. 3A, a proximal portion of 14 mm length is used for controlling heat transfer and that an outer tube diameter of 150 μm is used. Using for example stainless steel as a material an electric conductivity of $1.4 \times 10^6$ Sim may be assumed, From the assumed numbers an electric resistance of 0.88 may be estimated. Thus, an electric current of approximately 2.4 A may be used for heating. Note that at the estimated resistance, a low voltage level ("a few volts") may be used for generating the required heating power. Thus, the design allows for safe implementation inside a cryoablation device. For (continuously) adjusting the current between limits, pulse width modulation may be applied, Here, for avoiding electromagnetic interference with other components, it may be of advantage to remove ripple from the applied current by using inductors and/or capacitors as known in the art.

For the exemplary embodiment shown in FIG. 6 the three-stage cascade control structure 703 is the preferred pathway for controlling cooling power via measurement of a catheter temperature. However, in some exemplary embodiments the central control unit 701 can be used for additionally adjusting a preconditioning temperature via proper selection of the preset value 740. As it was described in the above numerical example 1, this may increase the range of control.

Similar as for the preconditioning temperature, the central control unit 701 may also adjust a high-pressure level via a control loop containing a negative feedback summation 746, a pressure controller 748, a pressure plant 749 relating a pressure command 745 to an actual pressure as measured, e.g., by sensor 181 in FIG. 5, As was described in more detail above, the set-pressure 781 may be set to a predefined value or may be adapted within a relatively narrow range.

In an exemplary embodiment the control structure 700 may be modified by essentially replacing the three-stage cascade structure 703 by a system using temperature dependent physical properties (as depicted in FIG. 4A) for providing a certain adjustment of flow to an actual precooling level. In such an exemplary embodiment the central control unit 701 may use operational parameters such as a catheter temperature 144 and/or a mass flow rate 170 and may further adjust preconditioning temperature 140 via a variable set-value 740 for compensating variations in ambient conditions and tank level. In yet another exemplary embodiment also the high-pressure level 181 may be adjusted via output 781 for obtaining a broader range of control.

In yet another exemplary embodiment, a pre-adjustment of flow may be obtained by designing the heat exchanger with proper dimensions and material parameters but without elements of significant temperature dependent geometric variation and without the use of an external heat flow for adjusting bypass flow. In such an exemplary embodiment the central control unit 701 may use operational parameters such as a catheter temperature 144 and/or a mass flow rate 170 and may further set preconditioning temperature 140 via a variable set-value 740 for compensating (in particular moderate) variations in ambient conditions and tank level. In yet another exemplary embodiment also the high-pressure 181 may be adjusted within sufficiently narrow limits via output 781 for obtaining a sufficient range of stable operation. In such a setting a precondition temperature 140 may be adjusted such that a distal shaft temperature 144 remains within a range of moderate rewarming from a boiling temperature. Using for example nitrous oxide as a refrigerant, a target distal shaft 144 temperature of e.g. −50° C. to −10° C. may be used.

In addition to the input parameters as described above, the central control unit 701 may monitor ambient parameters, such as an ambient temperature $T_a$ and/or a tank pressure $p_T$. An ambient parameter bus 702a may input estimates of ambient conditions to the block 701. Furthermore, the cryoablation system may monitor system parameters, such as a low-pressure recording (sensor 172 in FIG. 5), a temperature in a refrigerant supply or return line, etc. A system parameter bus 704 may input estimates of system conditions to the block 701. Each of these ambient and/or parameters can be used for control/adjustment of cooling power and for a safety system ensuring the functional safety of the cryoablation systems.

Furthermore, user inputs 705 may be assessed as an input to the central control block. Such user inputs may be desired temperatures, flow rates, pressure levels, power levels or the like.

Figure 7:
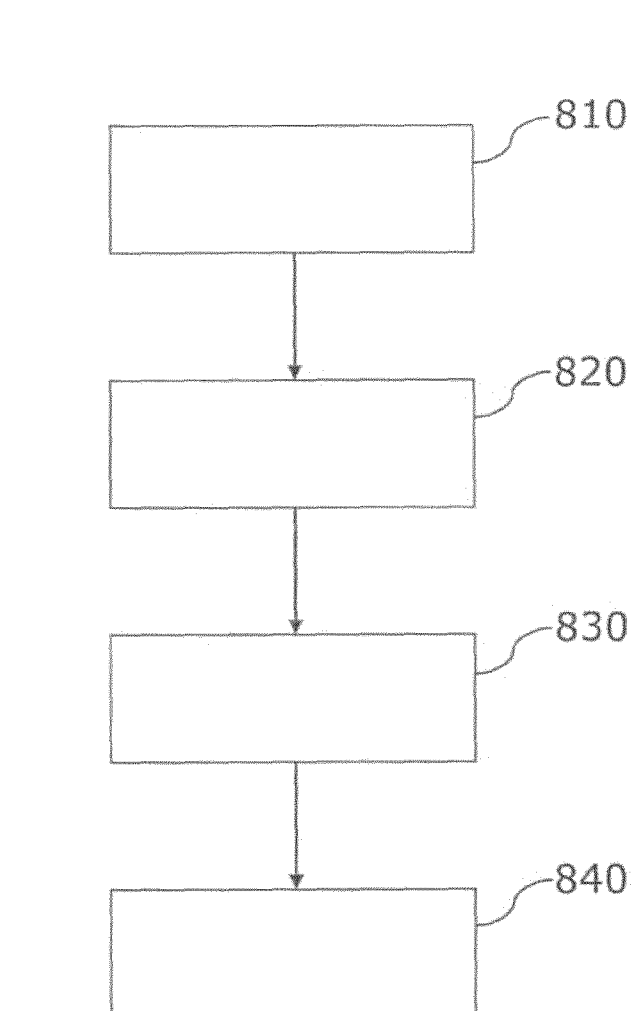
FIG. 7 shows a flow chart of a method according to an exemplary embodiment of the present disclosure.

FIG. 7 shows a block diagram of a method 800 according to an exemplary embodiment. The method 800 corresponds to operation of the cryoablation systems discussed above and begins at 810 by receiving an input flow of refrigerant fluid. At 820, the input flow is split into a therapeutic flow portion and a precooling flow portion. At 830, the therapeutic flow portion is precooled by applying an adjustable precooling power from the precooling flow portion to the therapeutic flow portion utilizing a heat exchanger. Finally, at 840, the precooled therapeutic flow portion is guided towards a cryo-applicator.

It is noted that the term "comprising" does not exclude other elements or steps and the use of the articles "a" or "an" does not exclude a plurality. Elements described in association with different exemplary embodiments may also be combined. It is further noted that reference signs in the claims are not to be construed as limiting the scope of the claims.

The invention claimed is:

1. A cryoablation catheter assembly, the assembly comprising:
   an inlet for receiving an input flow of refrigerant fluid,
   a cryo-applicator,
   a flow splitter configured to split the input flow into a therapeutic flow portion and a precooling flow portion,
   a precooling arrangement configured to precool the therapeutic flow portion and guide the precooled therapeutic flow portion towards the cryo-applicator,
   wherein the precooling arrangement comprises a heat exchanger configured to apply an adjustable precooling power from the precooling flow portion to the therapeutic flow portion,
   wherein the heat exchanger comprises a boiling chamber, a conduit configured to guide the precooling flow portion from the flow splitter to the boiling chamber, and a heat transfer structure in thermal contact with the boiling chamber and configured to guide the therapeutic flow portion,
   wherein the conduit comprises a microtube having a flow impedance selected to maintain a ratio between the precooling flow portion and the input flow within a predetermined range, and
   a closing structure is arranged between the conduit and the boiling chamber, the closing structure being configured to adjust a flow cross-section in dependency of temperature.

2. The assembly according to claim 1, wherein the microtube has a cross-sectional area of 0.1 mm² or less.

3. The assembly according to claim 1, wherein the microtube has a length of at least 5 mm.

4. The assembly according to claim 2, wherein the microtube has an inner diameter of 90 μm and a length of 40 mm.

5. The assembly according to claim 1, wherein the precooling arrangement comprises a temperature adjustment device configured to adjust the temperature of the precooling flow portion within the conduit.

6. The assembly according to claim 5, wherein the temperature adjustment device comprises an adjustable electric heating unit configured to heat the conduit.

7. The assembly according to claim 5, wherein the temperature adjustment device comprises an adjustable heating and cooling unit configured to selectively heat and cool the conduit.

8. The assembly according to claim 5, further comprising at least one temperature sensor arranged and configured to provide a temperature signal indicative of the temperature of the therapeutic flow portion, wherein the temperature adjustment device is configured to adjust the temperature of the precooling flow portion within the conduit in dependency on the temperature signal.

9. The assembly according to claim 8, wherein the at least one temperature sensor comprises a first temperature sensor arranged in or on the heat exchanger and adapted to sense a temperature of the precooled therapeutic flow portion leaving the heat exchanger, and/or wherein the at least one temperature sensor comprises a second temperature sensor arranged and adapted to sense a temperature of the precooling flow portion.

10. The assembly according to claim 8, wherein the at least one temperature sensor comprises a third temperature sensor arranged and adapted to sense a temperature of the therapeutic flow portion within the cryo-applicator.

11. The assembly according to claim 8, wherein the at least one temperature sensor comprises a fourth temperature sensor arranged and adapted to sense a temperature of the therapeutic flow portion leaving the cryo-applicator.

12. The assembly according to claim 1, wherein the heat transfer structure has an elongate shape and extends through the boiling chamber.

13. The assembly according to claim 1, wherein the heat exchanger is configured as a counter flow heat exchanger or as a parallel flow heat exchanger.

14. The assembly according to claim 1, further comprising a handle, wherein the precooling arrangement is arranged within the handle.

15. A cryoablation system, the system comprising:
   a cryoablation catheter assembly, said cryoablation catheter assembly comprising:
   an inlet for receiving an input flow of refrigerant fluid, a cryo-applicator,
   a flow splitter configured to split the input flow into a therapeutic flow portion and a precooling flow portion,
   a precooling arrangement configured to precool the therapeutic flow portion and guide the precooled therapeutic flow portion towards the cryo-applicator,
   wherein the precooling arrangement comprises a heat exchanger configured to apply an adjustable precooling power from the precooling flow portion to the therapeutic flow portion,
   wherein the heat exchanger comprises a boiling chamber, a conduit configured to guide the precooling flow portion from the flow splitter to the boiling chamber, and a heat transfer structure in thermal contact with the boiling chamber and configured to guide the therapeutic flow portion, and wherein the conduit comprises a microtube having a flow impedance selected to maintain a ratio between the precooling flow portion and the input flow within a predetermined range, a console configured to supply a flow of refrigerant fluid to the inlet of the cryoablation catheter assembly, wherein the console comprises a preconditioning unit configured to adjust a specific enthalpy of the refrigerant fluid to a predetermined value, and a closing structure is arranged between the conduit and the boiling chamber, the closing structure being configured to adjust a flow cross-section in dependency of temperature.

16. The system according to claim 15, further comprising a controller configured to determine the predetermined value in dependency on at least one measured temperature.

* * * * *